United States Patent
Bütikofer et al.

(10) Patent No.: US 7,303,544 B2
(45) Date of Patent: Dec. 4, 2007

(54) CATHETER HEAD WITH CLOSEABLE SEAL ELEMENT

(75) Inventors: Markus Bütikofer, Münsingen (CH); Rudolf Zihlmann, Langnau (CH); Simon Scheurer, Bern (CH)

(73) Assignee: Disetronic Licensing AG, Burgdorf (CH)

( * ) Notice: Subject to any disclaimer, the term of this patent is extended or adjusted under 35 U.S.C. 154(b) by 0 days.

(21) Appl. No.: 11/140,486

(22) Filed: May 27, 2005

(65) Prior Publication Data

US 2006/0015063 A1 Jan. 19, 2006

Related U.S. Application Data

(63) Continuation of application No. PCT/EP2003/012003, filed on Oct. 29, 2003.

(30) Foreign Application Priority Data

Nov. 29, 2002 (DE) ................. 102 55 817

(51) Int. Cl.
*A61M 11/00* (2006.01)
(52) U.S. Cl. ................. 604/93.01; 604/164.02
(58) Field of Classification Search ............. 604/93.01, 604/164.07, 180, 283, 167.03, 167.06, 33, 604/288.03, 288.04
See application file for complete search history.

(56) References Cited

U.S. PATENT DOCUMENTS

| 5,522,803 | A | | 6/1996 | Teissen-Simony |
| 5,968,011 | A | * | 10/1999 | Larsen et al. ......... 604/288.02 |
| 6,017,328 | A | | 1/2000 | Fischell et al. |
| 6,056,718 | A | * | 5/2000 | Funderburk et al. ..... 604/93.01 |
| 2002/0161332 | A1 | * | 10/2002 | Ramey ................. 604/164.07 |

FOREIGN PATENT DOCUMENTS

| DE | 198 21 723 | 11/1999 |
| DE | 199 22 350 C1 | 12/2000 |
| DE | 100 35 342 A1 | 2/2002 |
| DE | 201 10 059 U1 | 9/2002 |
| DE | 101 17 285 A1 | 11/2002 |
| EP | 0 704 227 A2 | 4/1996 |
| EP | 1 016 431 B1 | 6/2004 |
| WO | WO 02/074381 A2 | 9/2002 |
| WO | WO 02/081012 A2 | 10/2002 |
| WO | WO 02/083206 A2 | 10/2002 |
| WO | WO 03/075980 | 9/2003 |

* cited by examiner

*Primary Examiner*—Nicholas D. Lucchesi
*Assistant Examiner*—Laura Bouchelle
(74) *Attorney, Agent, or Firm*—Dorsey & Whitney LLP

(57) ABSTRACT

A catheter head for medical and pharmaceutical applications, including a base body which may be positioned on organic tissue and a connecting body, serving as fluid connector for the base body, which has a fluid channel to form the fluid connection. The base body and the connecting body are detachably connected to each other and the base body includes: a) a housing b) a cannula, extending from the housing for introduction into the tissue, c) a seal element, retained by the housing, which has a connector face on which or by means of which the fluid channel of the connecting body may be hydraulically connected to the cannula, and d) a closing element, mounted on the housing which may be displaced relative to the sealing element and seals the sealing face of the sealing element in a closed position and opens the connecting body for the fluid channel in an open position.

31 Claims, 9 Drawing Sheets

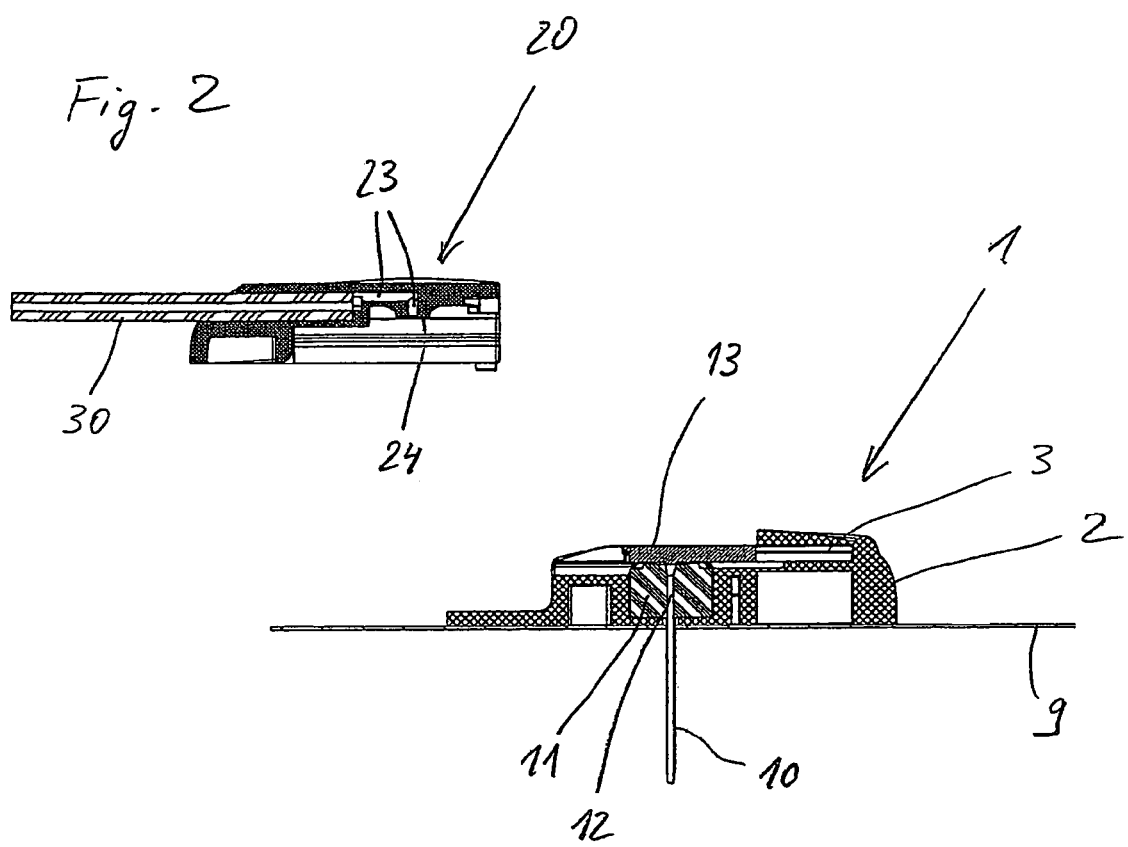

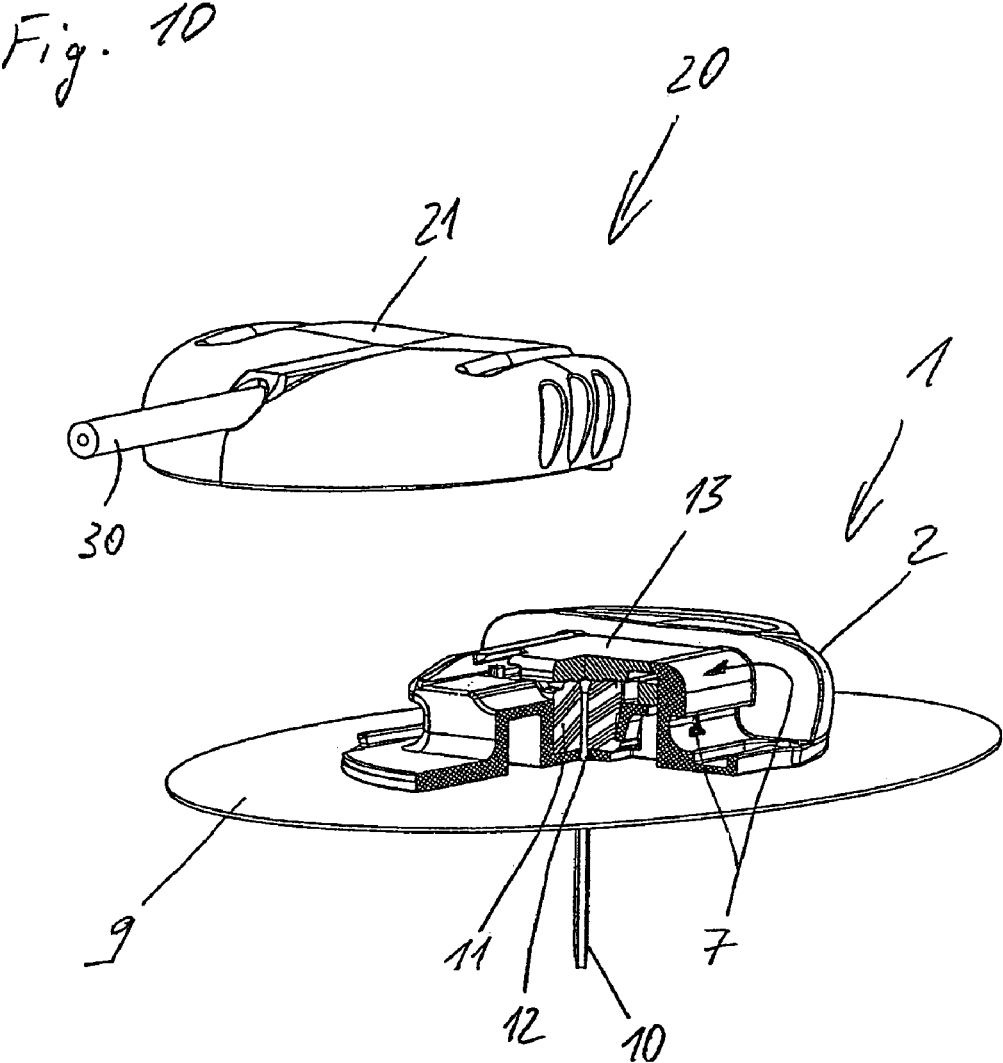

CATHETER HEAD WITH CLOSEABLE SEAL ELEMENT

CROSS-REFERENCE TO RELATED APPLICATION(S)

This application is a continuation of International Application No. PCT/EP2003/012003, filed on Oct. 29, 2003, which claims priority to German Application No. 102 55 817.5, filed on Nov. 29, 2002, the contents of which are incorporated by reference in their entirety herein.

BACKGROUND

The present invention relates devices and methods for administering, dispensing or delivering substances, and to such devices and methods used in the medical field. More particularly it relates to catheters, infusion devices and the like, including a catheter head for therapeutic or pharmaceutical uses. The catheter head can be part of an infusion set, or it can form an infusion set in combination with a catheter and/or one or more other fluid-conveying elements or components.

A catheter head, as is known from DE 198 21 723 C, for example, is made up of a base body which can be positioned on organic tissue, for example on human skin, and of a connecting body via which a catheter, serving for delivery of fluid, is connected to the base body. Protruding from an underside of the base body, or laterally therefrom, there is a cannula which is inserted into the tissue and is fixed in the inserted state by the positioning of the base body on the tissue. The base body serves as a connector for the cannula. A septum is formed in a housing of the base body in order to seal off the cannula hermetically from the outside. The connecting body comprises a connecting needle which is connected, via an internal fluid channel of the connecting body, to the catheter or to other fluid-conveying parts of an infusion system. When the connecting body is connected to the base body, the connecting needle pierces the septum, so that the internal fluid channel of the connecting body is connected fluidically to the cannula by way of the connecting needle and an internal fluid channel of the connecting body. The connecting body can be separated from the base body and repeatedly connected to the base body. Each time the connection is established, the connecting needle pierces the septum. The septum has the property of hermetically sealing off the cannula from the outside when the connecting needle is withdrawn from the septum upon release of the connection between the base body and the connecting body.

SUMMARY

In the case of a catheter head for medical and pharmaceutical applications, it is an object of the invention to improve the sealing of a cannula which, when in use, is inserted into tissue.

The present invention relates to a catheter head for medical and pharmaceutical applications. It may be used in therapeutic applications for administration of a liquid product, for example an infusion liquid. A prominent example of such an infusion liquid is insulin in the treatment of diabetes. In principle, however, the catheter head can also be used for diagnostic purposes for removing fluid from organic tissue and analyzing it for specific diagnostic purposes.

The catheter head comprises a base body, which can be positioned on organic tissue, preferably the human skin, and a connecting body which is or can be connected releasably to the base body. The connecting body can be connected to a catheter or to another element suitable for conveying fluid and forms a fluid connection with at least one fluid channel through which a fluid, in particular a liquid, can flow from the catheter, or from the other element suitable for conveying fluid, to the base body or in the reverse direction. The connecting body thus serves as fluid connector for the base body. The base body, the connecting body and a catheter connected to the connecting body, with a conventional attachment end, preferably already form an infusion set which is sold on the market as such.

The word "body" is intended to signify that the parts thus designated can be handled as a single part. The units designated as "body" can be in one piece, but they do not have to be. In some preferred embodiments, the connecting body can be in one piece, but the base body comprises at least one component which is movable relative to the rest of the body.

The base body comprises a housing, a cannula protruding from the housing, and a seal element which is held by the housing. The seal element is preferably in one piece, but can instead easily be made up of a plurality of seal element sections. An underside of the housing is prepared for positioning on the tissue, for example by an adhesive pad being arranged in a conventional manner on the underside of the housing. The cannula can in particular protrude from the underside of the housing. However, it can, for example, also protrude from another side of the housing adjoining said underside. The cannula can itself be a puncture needle. However, the cannula is preferably flexible and is introduced into the tissue by means of a puncture needle, in which case, after introduction of the cannula, the puncture needle is removed again and only the flexible cannula remains in the tissue. By positioning and securing the base body on the tissue, the inserted cannula is held in the tissue and fixed in this sense.

The seal element has a connector face which, when the connecting body is connected to the base body, is directed toward the connecting body or, more precisely, toward the connector end of the fluid connection of the connecting body. The fluid connection of the connecting body can be placed in fluidic communication with the cannula of the base body at the connector face or via the connector face of the seal element. When the base body and the connecting body are connected to one another, the seal element seals the connection made between the connecting body and the cannula from the outside, so that the fluid can flow without any loss from the connecting body to the cannula and/or in the reverse direction.

According to the present invention, the base body also comprises a closure element supported movably by the housing of the base body. The closure element can be moved relative to the seal element such that, in a closure position, it seals off the connector face of the seal element and, in an open position, it opens the fluid channel of the connecting body. It can preferably be moved back and forward between the closure position and the open position. The movement of the closure element can be a pivot movement or rotation movement, for example. In some embodiments, the movement is preferably a translation movement and particularly preferably a linear displacement movement. In its closure position, the closure element is pressed with a suitable pressing force against the connector face of the seal element, so that a hermetic seal is obtained between the cannula and the environment when the connecting body is detached from the base body.

An advantage of the closure element according to the invention is that the seal element does not need to be a septum of the conventional kind which is pierced by a connecting needle and which, even after repeated piercing and with the connecting needle withdrawn, has to seal the cannula of the base body hermetically, i.e. in a sterile manner, from the outside. However, configuring the seal element in such a conventional manner and forming the connecting body with a connecting needle should not be ruled out. By virtue of the closure element according to the invention, however, the seal element advantageously does not have to meet such requirements. A further advantage is that the connecting body does not need to have a connecting needle which may pose a risk of injury. Its fluid channel can advantageously open out in a short outlet nozzle.

In a preferred embodiment, the seal element has a permanent passage extending from the cannula as far as the connector face of the seal element. In this configuration, the connecting body preferably has no connecting needle. In the connected state of connecting body and base body, the connecting body instead presses with a connector end of its fluid channel against the connector face of the seal element in order to create the leaktight and sterile connection, necessary for medical applications, between the fluid channel of the connecting body and the cannula of the base body. Accordingly, the seal element is not damaged for the purpose of creating the fluidic connection, as necessarily happens when piercing conventional septums. However, if the seal element of the catheter head according to the invention is one such septum and the connecting body accordingly has a connecting needle, the closure element according to the invention, in its closure position, nevertheless provides improved sealing of the cannula from outside.

As regards the seal element provided with a permanent passage, it should also be noted that the passage preferably extends right through the seal element, and the connector face is preferably formed on that side of the seal element remote from the cannula. In principle, however, the connector face can also be formed by another side of the seal element. The connector face could, for example, adjoin the side from which the cannula protrudes. In principle, the connector face could even be formed on the same side as the cannula, which would however lead to a structurally difficult configuration on sides of the base body and of the connecting body. Instead of a passage, the seal element for creating the fluidic connection between connecting body and cannula can have a channel open to one end. Such a channel open at one end can also be formed by the housing, and in such a configuration the seal element seals off the open end of the channel.

In preferred embodiments, the seal element and the cannula are formed in one piece, preferably made of plastic by injection molding. In an alternative configuration, the cannula and the seal element can be produced separately. In such a configuration, the cannula can be joined to the housing and connected to it, for example by being inserted into the housing and extending beyond the underside of the latter. Likewise, a separately produced cannula could be fitted into a seal element, protruding through this at least on one side, for example by fitting the cannula in a passage in the seal element and thereby securing it. It is also quite conceivable to produce the cannula in one piece with the housing, for example in a plastic injection molding process.

Unwanted movement of the closure element from the closure position is already countered by the pressing force needed for sealing the connector face of the seal element. With an appropriate construction, the pressing force is on its own sufficient to hold the closure element sufficiently securely in the closure position, but it is preferable if the closure element in the closure position is in blocking (or locking) engagement with the housing of the base body so that, by means of form-fit locking or blocking, it is ensured that the closure element cannot accidentally move out of the closure position. For a detachable, form-fit blocking engagement or a detachable, form-fit and force-fit blocking engagement, the housing of the base body and the closure element each have at least one blocking element. The at least one blocking or locking element of the closure element and the at least one blocking or locking element of the housing are preferably locked together in the blocking engagement. The locking is effected preferably automatically by elasticity forces when the closure element reaches its closure position.

In some embodiments, the connecting body and the closure element are preferably configured such that, when the connection is made between the base body and the connecting body, the closure element is automatically moved from the closure position to the open position. It is preferred if the connecting body simply drives the closure element with it in the movement which the connecting body makes relative to the base body in order to establish the connection. Upon connection of the connecting body to the base body, the connecting body and the closure element execute the same movement relative to the base body from the closure position of the closure element to its open position.

In order to reliably ensure the sealing of the connector face of the seal element, the closure element should be moved automatically into the closure position when the connecting body is detached from the base body. In such a preferred configuration, the closure element and the connecting body are accordingly coupled to one another when the base body and the connecting body are connected to one another. The coupling is preferably obtained automatically, i.e. without the need for special maneuvers for its production. Like the preferably automatically obtained movement of the closure element from the closure position to the open position, the coupling is likewise a driving engagement which has the effect that the connecting body drives the closure element along with it when it is detached from the base body.

Although a coupling between the connecting body and the closure element is already advantageous for the purpose of moving the closure element automatically either from the closure position to the open position or, conversely, from the open position to the closure position, in some embodiments, it is preferable if the connecting body and the closure element are coupled to one another in such a way that the movement of the connecting body relative to the base body produces both the movement from the closure position and also the movement into the closure position.

BRIEF DESCRIPTION OF THE DRAWINGS

FIG. 2 shows a connecting body of the catheter head before connection,

FIG. 3 shows a base body of the catheter head before connection,

FIG. 10 shows the connecting body in a perspective view, and FIG. 11 shows the base body in a perspective view and in a cross section along the axis of symmetry and a cross section at right angles to the axis of symmetry.

DETAILED DESCRIPTION OF THE DRAWINGS

Figure 1:
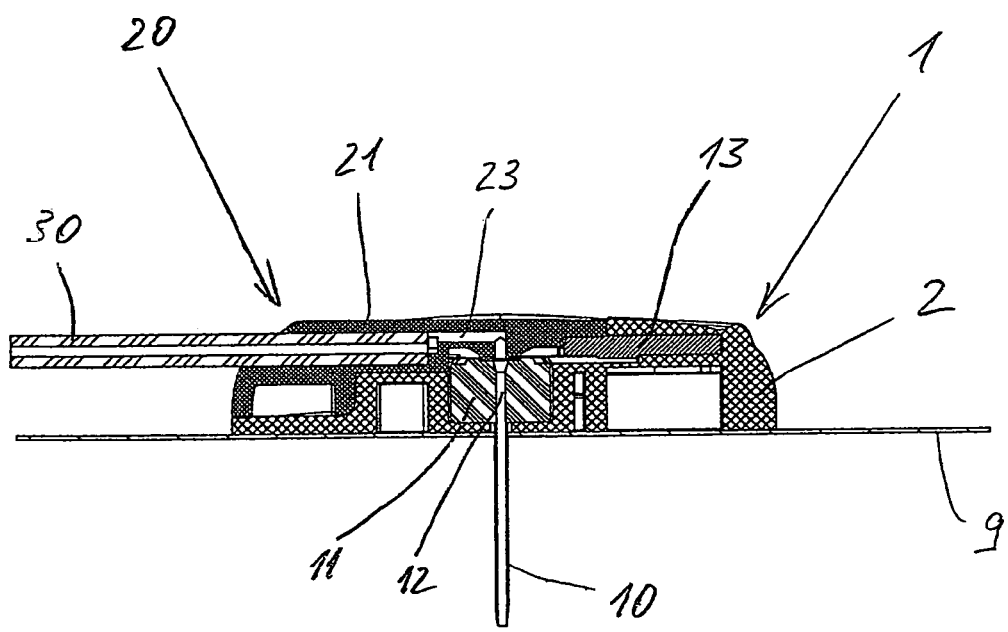
FIG. 1 shows a catheter head in longitudinal section along an axis of symmetry.

FIG. 1 shows a catheter head in longitudinal section. The catheter head is made up of a base body 1 and a connecting body 20 which are mechanically and fluidically connected to one another in a detachable manner. The catheter head forms an infusion set in combination with a delivery catheter 30 attached to the connecting body 20 and having at its free end (not shown) a coupling for attachment to a pump, for example. The infusion set can be used in particular for administering a liquid medicament. In the illustrative embodiment, the catheter head is used for subcutaneous administration of insulin, for example. For administration, the catheter head has a cannula 10 which is introduced under the skin, into tissue layers adjacent to the skin. The cannula 10 is inserted until the catheter head lies with its underside on the skin surface, so that the catheter head is positioned on the skin and the cannula 10 in the tissue.

The base body 1 comprises a housing 2, the cannula 10, a seal element 11 for the cannula 10, a closure element 13 for the seal element 11, and an adhesive pad 9. The housing 2 is made in one piece of plastic by injection molding. The adhesive pad 9 is secured on an underside of the housing 2 which at the same time also forms the underside of the catheter head, and said adhesive pad 9 serves in a known manner for securing the catheter head on the skin or, in applications different than the illustrative embodiment, on corresponding tissue surfaces. The cannula 10 protrudes from the underside of the housing 2 and passes through the adhesive pad 9. It opens into the housing 2 in a housing space in which the seal element 11 is arranged.

The seal element 11 has a passage 12 which opens at the underside of the housing 2 into the cannula 10. The passage 12 extends right through the seal element 11 and opens out on a connector face of the seal element 11 directed away from the cannula 10, which connector face, in the illustrative embodiment, is the top face of the seal element 11 directed away from the cannula 10. The seal element 11 as such seals off the fluidic connection between the connecting body 20 and the cannula 10 by tightly surrounding the connector end of the connecting body 20 and, with its permanent passage 12, itself connects the connector end of the connecting body 20 to the cannula 10.

In the connected state shown in FIG. 1, a fluidic connection exists between the delivery catheter 30 and the cannula 10. The fluidic connection is formed by a fluid channel 23 of the connecting body 20 and the passage 12 of the seal element 11. The fluid channel 23 opens out on an underside of the connecting body 20 which, for the opening out of the fluid channel 23, forms an outlet nozzle 24 there (FIG. 2). In the connected state, the outlet nozzle 24 surrounds the mouth of the passage 12 and is pressed against the connector face of the seal element 11 with a pressing force which is as low as possible, but still sufficient for the desired sealing action, in order to connect the fluid channel 23 to the passage 12 in a sealed manner.

The closure element 13 is supported in a movable manner by the housing 2 of the base body 1. The closure element 13 can be displaced linearly between an open position, which it assumes in the connected state (FIG. 1), and a closure position, which it assumes in the unconnected state (FIG. 3). The direction of mobility is parallel to the connector face of the seal element 11.

In its closure position, the closure element 13 forms a cover for the seal element 11, with which cover the passage 12 is sealed off from the outside at the connector face of the seal element 11, so as to avoid contamination of the cannula 10 when the cannula 10 is inserted into the tissue. To increase the sealing effect, the closure element 13, as will be seen from FIG. 1, can have a raised area on its underside directed toward the connector face of the seal element 11, with which raised area it is pressed against the connector face of the seal element 11 in the closure position around the mouth of the passage 12.

Upon connection of the connecting body 20, the closure element 13 is pushed into a receiving compartment 3 (FIG. 3) of the housing 2 of the base body 1. This is effected by means of the connecting body 20 which, for this purpose, is pushed onto the housing 2 of the base body 1 in the direction of displaceability of the closure element 13. When pushed on, the connecting body 20 presses the closure element 13 into the open position shown in FIG. 1. Upon disconnection, the connecting body 20 is drawn back from the housing 2 of the base body 1 counter to the direction in which it is pushed on and, in this movement of withdrawal, it also drives the closure element 13 with it into the closure position shown in FIG. 3.

The housing 2 and the closure element 13 form a linear guide for the displacement movement of the closure element 13. The housing 2 and the connecting body 20 form a further linear guide for the push-on and withdrawal movement of the connecting body 20 during connection and disconnection. The linear guide for the closure element 13 is formed by the two oppositely directed side walls 15 of the closure element 13 (FIG. 4) and one of two guide tracks 4 (FIG. 6) of the housing 2 facing each other. The linear guide for the connecting body 20 is formed by side walls of the housing 2 which form guide tracks 7 (FIG. 11) and by corresponding matching walls 26 of the connecting body 20 (FIG. 5).

Both linear guides, namely the one for the closure element 13 and the one for the connecting body 20, are slide guides. The slide guide for the connecting body 20 is also configured in such a way that the connecting body 20, when pushed onto the base body 1, centers itself with respect to the guide tracks 7 in order to make the pushing-on movement easier.

Figure 4:
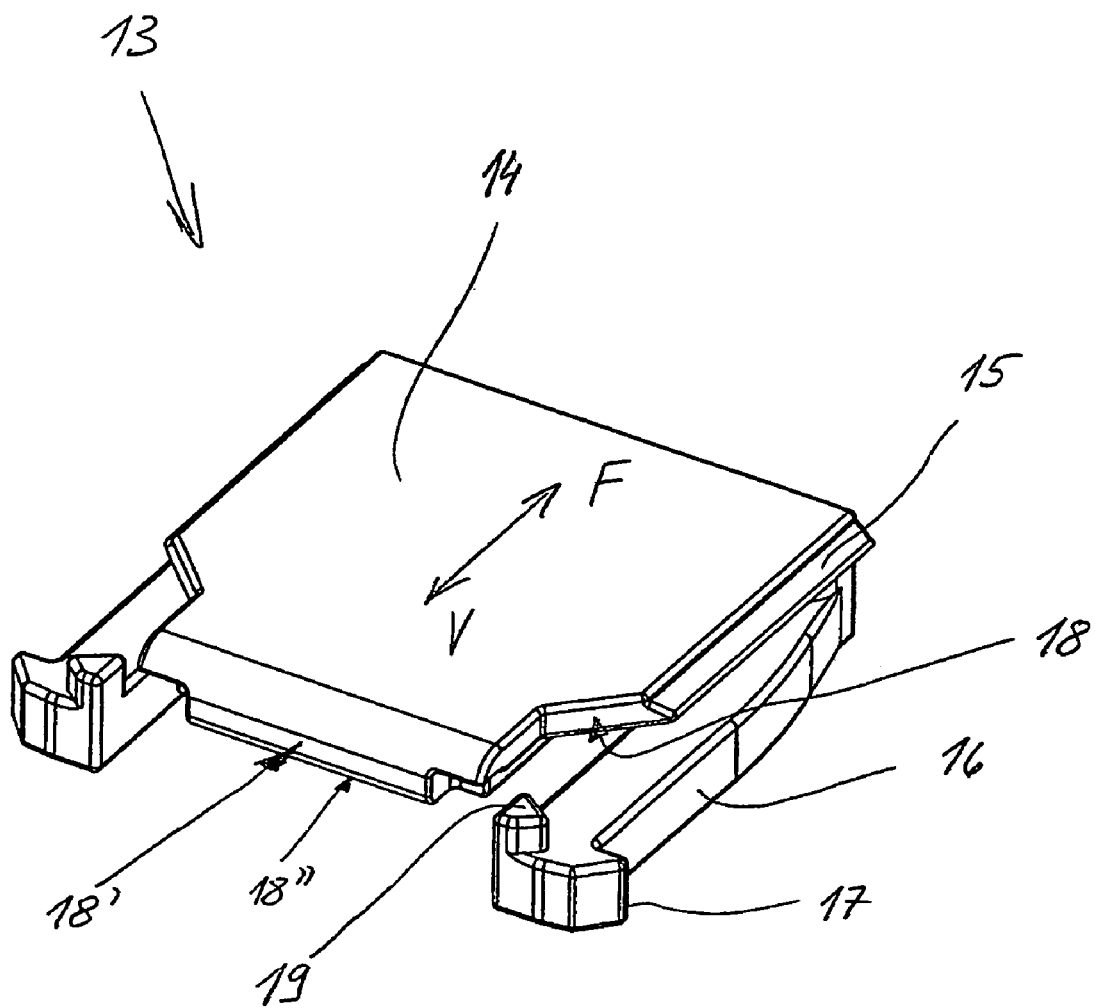
FIG. 4 shows a closure element of the catheter head in a separate view.
Figure 5:
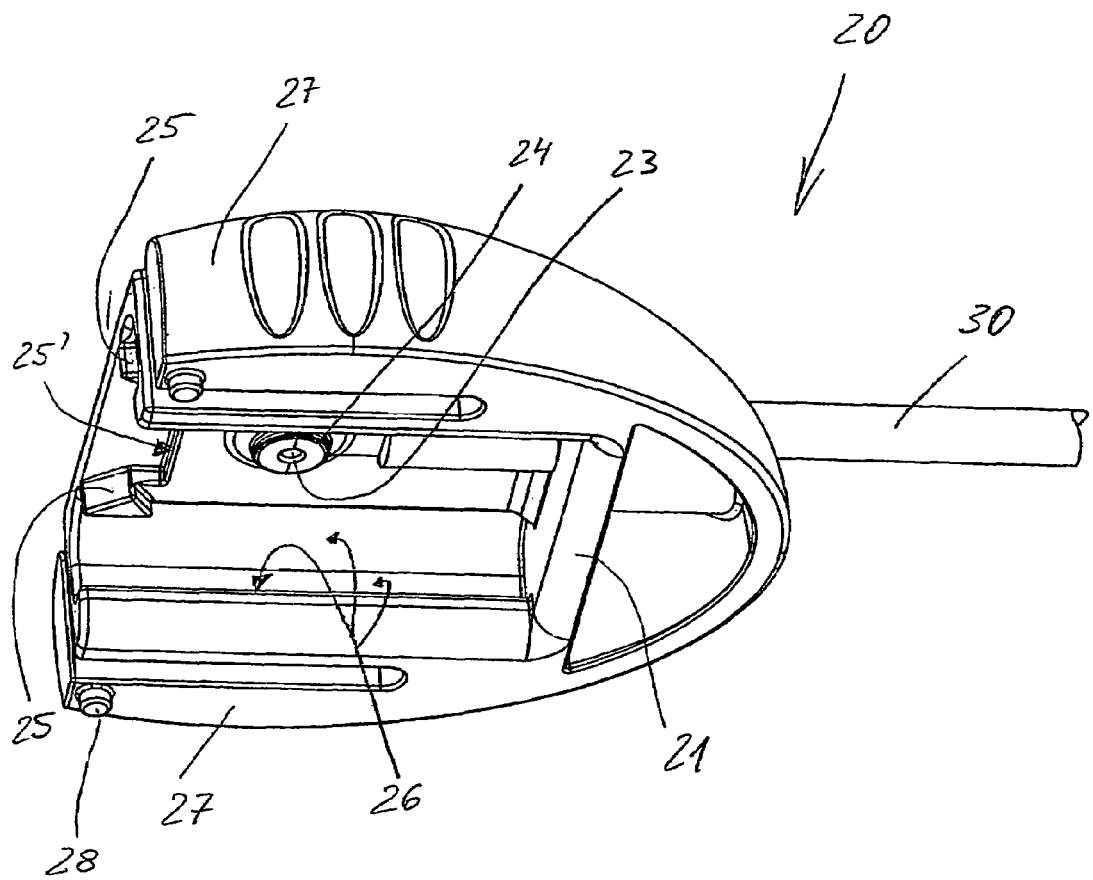
FIG. 5 is a perspective view of the underside of the connecting body of the catheter head.

FIG. 4 shows the closure element 13 separately, in a perspective view looking toward its top face. The closure element 13 has a main body 14 which with its underside tightly closes off the passage 12 of the seal element 11 in the closure position. The two opposite directions of movement of the closure element 13 are shown in FIG. 4, where the direction leading to the open position is designated by F and the direction leading to the closed position is designated by V.

Two snap-in catches 16 protrude in direction V from the front end of the main body 14 as seen with reference to direction F. The snap-in catches 16 are connected to the main body 14 in a flexurally elastic manner transversely with respect to the direction of mobility of the closure element 13. The two snap-in catches 16 can be bent toward one another counter to elastic restoring forces via their rear ends in relation to the direction F. FIG. 4 shows the two snap-in catches 16 in the released state. Each of the snap-in catches 16 forms a snap-in hook by means of the free ends of said snap-in catches 16 each having an outwardly directed projection 17. In the closure position of the closure element 13, the snap-in hooks formed in each case by one of the snap-in catches 16 and the projections 17 thereof hook onto the housing 2 of the base body 1, so that the closure element 13 in the closure position is prevented from moving from the closure position in the direction F to the open position. The snap-in hooks 16, 17 therefore form blocking, lock or locking elements of the closure element 13. The blocking elements 16, 17 interact with in each case a set-back shoulder 5 of the housing 2. The shoulders 5 form the matching and/or complementary blocking, lock or locking elements of the housing 2 and can be seen in FIG. 6, for example. The blocking engagement between the two blocking elements 16, 17 and the matching blocking elements 5 is a catch engagement into which the flexurally elastic blocking elements 16, 17 snap in the closure position of the closure element 13 and from which they can be moved out counter to their elastic restoring forces.

A cam 19 also protrudes from the rear end of each of the snap-in catches 16, as seen in the direction F. The two cams 19 protrude transversely with respect to the plane of the flexural elasticity of the snap-in catches 16 from the top faces thereof. The cams 19 form in particular, as will be explained below, drivers for the closure element 13, which, upon disconnection of the connecting body 20, are in driving engagement with corresponding matching drivers of the connecting body 20. The cams 19 are, accordingly, drivers of the closure element 13 which are active in direction V.

The closure element 13 forms drivers 18 and 18' active in direction F, in this illustrative embodiment two drivers 18 and one driver 18'. Each of the drivers 18 and 18' is an abutment surface formed by the main body 14 on the rear face of the main body 14 pointing in direction V. When the connecting body 20 is pushed onto the base body 1, the connecting body 20 presses with corresponding matching surfaces against these drivers 18 and 18'. Upon connection, the matching surfaces form the drivers of the connecting body 20.

FIG. 5 shows the connecting body 20 on its own, in a perspective view looking toward its underside. The two drivers 25 of the connecting body 20 can be seen in particular. Each of the two drivers 25 is a cam which protrudes from the underside of a housing 21 of the connecting body 20 and protrudes toward the base body 1 upon connection and in the connected state. The outlet nozzle 24 forming the mouth of the fluid channel 23 can also be clearly seen. The catheter 30 is fitted into the housing 21 and connected cohesively to the housing 21, for example by adhesive bonding. In a preferred injection molding of the housing 21, the catheter 30 could, for example, also be encapsulated with the material of the housing 21.

Figure 6:
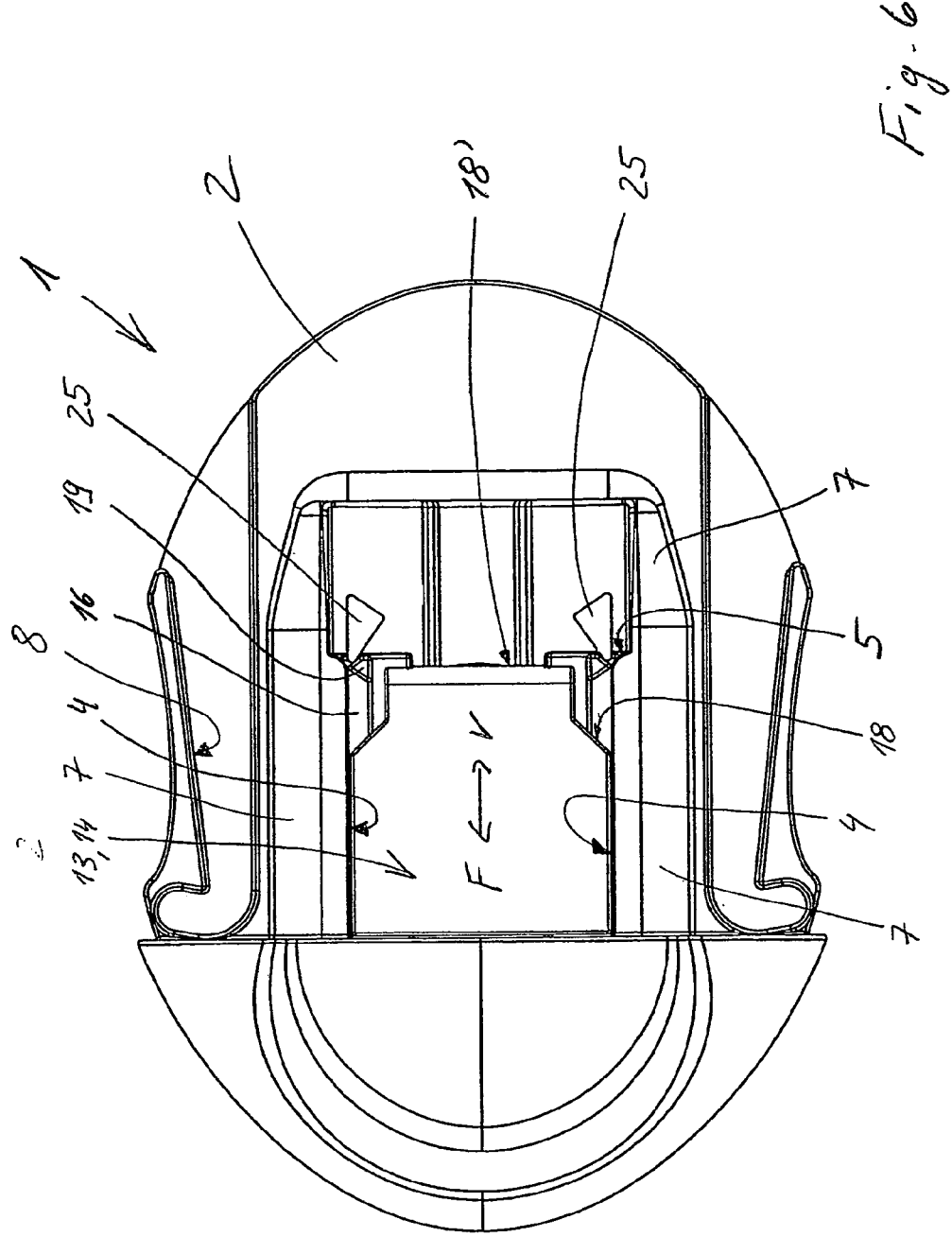
FIG. 6 is a plan view of the base body, with drivers of the connecting body shown prior to engagement with the closure element.
Figure 7:
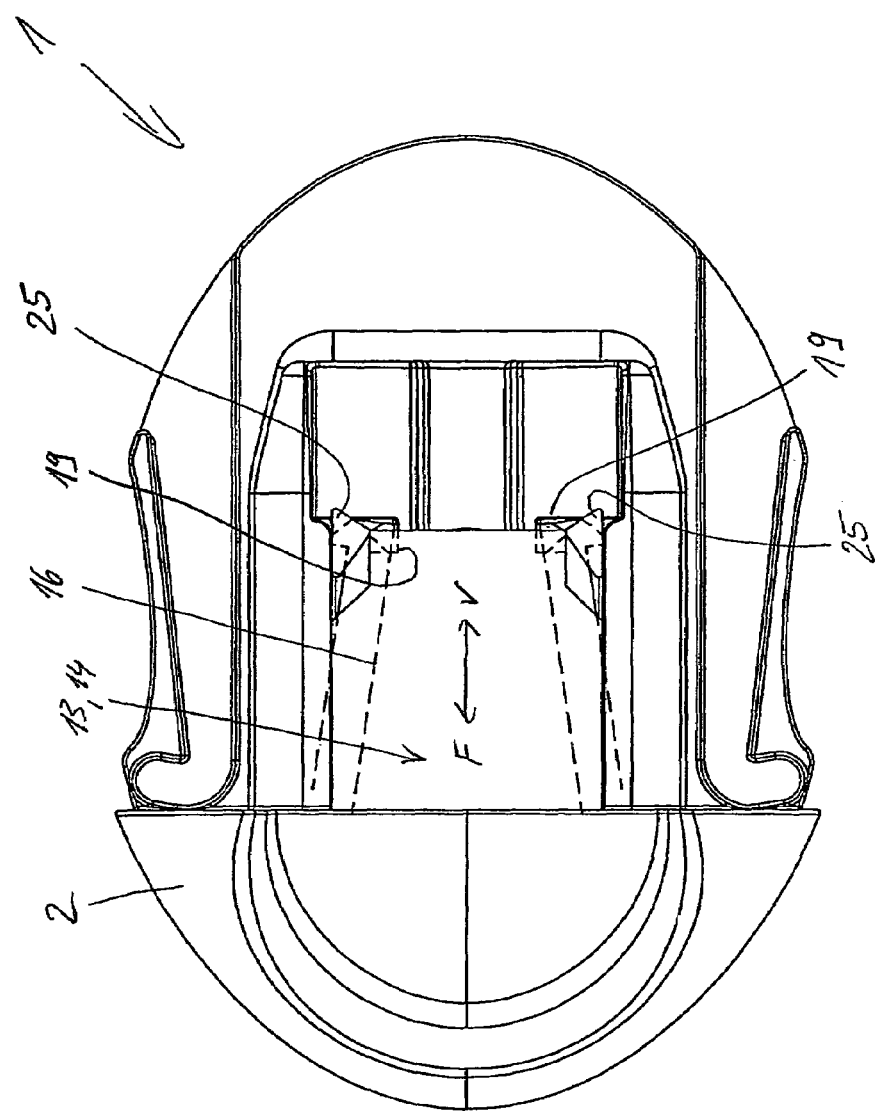
FIG. 7 shows the base body from FIG. 6, where the drivers of the connecting body elastically bend the drivers of the closure element.
Figure 8:
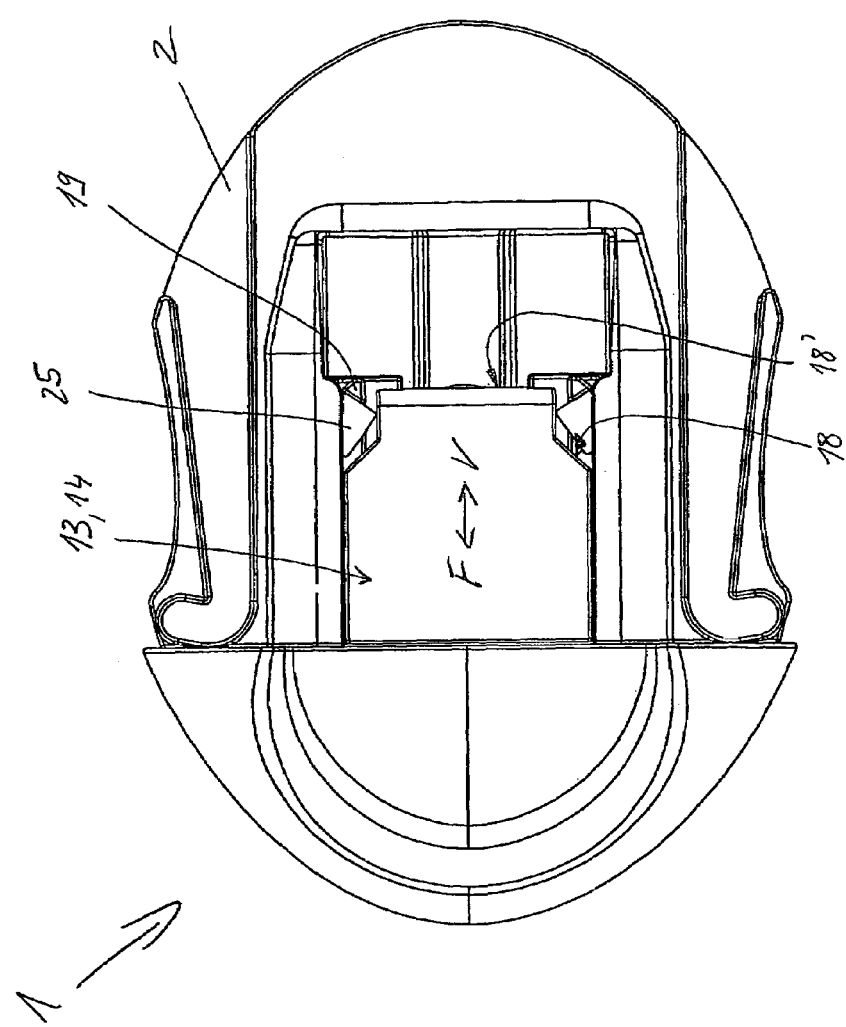
FIG. 8 shows the base body from FIGS. 6 and 7, where the drivers of the connecting body have been moved relative to the closure element and in each case into a position in which the drivers of the closure element have bent back again elastically.

FIGS. 6, 7 and 8 show, in sequence, the start of the connecting procedure, i.e. the start of pushing the connecting body 20 onto the base body 1. These figures are intended to illustrate the interaction of the drivers 25 of the connecting body 20 with the drivers 18 and 19 of the closure element 13. As regards the connecting body 20, only the two drivers 25 are shown, so as to reveal the snap-in catches 16 and the drivers 18 and 19 of the closure element 13.

In a first phase of the pushing-on movement, the connecting body 20 centers itself with respect to the base body 1 by virtue of the shape of the linear guide provided for the pushing-on procedure, i.e. its guide tracks 7. As soon as the centering procedure is completed and the connecting body 20 has slid tightly along the guide tracks 7, the front faces of the drivers 25 come into contact with the rear faces of the drivers 19 of the closure element 13. This state is shown in FIG. 6.

In the subsequent second phase of the pushing-on procedure, which is shown in FIG. 7, the two drivers 25 slide along the two drivers 19 of the closure element 13. In this sliding movement, the elastic snap-in catches 16 are bent inward toward one another. The snap-in catches 16 bent toward one another are shown by broken lines. In the plan view in FIG. 7, they are concealed by the main body 14 of the closure element 13. To permit or facilitate the sliding on the drivers 19, the front faces of the drivers 25 and the rear faces of the drivers 19 are ramp-shaped, so that they can slide onto one another in the manner of oblique planes. FIG. 7 shows the snap-in catches 16 at maximum flexion.

As the connecting body 20 is pushed on farther, its drivers 25 come before the drivers 19 of the closure element 13, as is shown in FIG. 8. The snap-in catches 16 are released again in the state shown in FIG. 8, i.e. they have bent back outward again elastically.

When pushed still farther on, the drivers 25 come into contact with the drivers 18 of the closure element 13 which are designed as abutment surfaces, so that, in the following third phase of the pushing-on procedure, the connecting body 20 slides against the closure element 13, pressing it in direction F into the open position. The open position of the closure element 13 is an abutment position, i.e. the closure element 13 in the open position has a front abutment face, pointed in direction F, abutting against a corresponding matching surface of the housing 2 of the base body 1. In the open position, the snap-in hooks 16, 17 snap into recesses of the housing 2 so that they are released. The closed position too is an abutment position in which, with respect to direction F, a rear surface 18" of the closure element, formed underneath the driver surface 18', abuts against a corresponding matching surface of the housing 2 of the base body 1.

As FIG. 8 also shows, the driving engagement, by which the closure element 13 is brought into the closure position upon disconnection of the connecting body 20, is also already established upon connection. The driving engagement active in direction V (FIG. 8) exists in fact between the drivers 25 of the connecting body 20 and the drivers 19 of the closure element 13 which were pushed by the drivers 25 in direction F upon connection. In the connected state, the driver pairs formed by the drivers 19 and 25 have surfaces which face one another and on which they are pressed against one another while being driven. These surfaces, pressed against one another during the driving upon disconnection, point obliquely in direction V and are parallel to one another. The inclination is dimensioned in such a way that the driving is safely effected, on the other hand the driving engagement is however automatically released when the closure element 13 has reached its closure position, but the connecting body 20 is further drawn off. The connecting body 20 is moved on the guides 7 of the base body 1 via the closure position of the closure element 13 a slight distance farther in direction V. When the closure element 13 has reached the closure position configured as abutment position, the drivers 25 push the drivers 19 of the closure element 13 in direction V, so that the snap-in catches 16 are bent elastically toward one another again and finally the driving engagement active in direction V is released. The snap-in catches 16 snapping back hook with their projections 17 again behind the force shoulders 5 of the housing 2.

Figure 9:
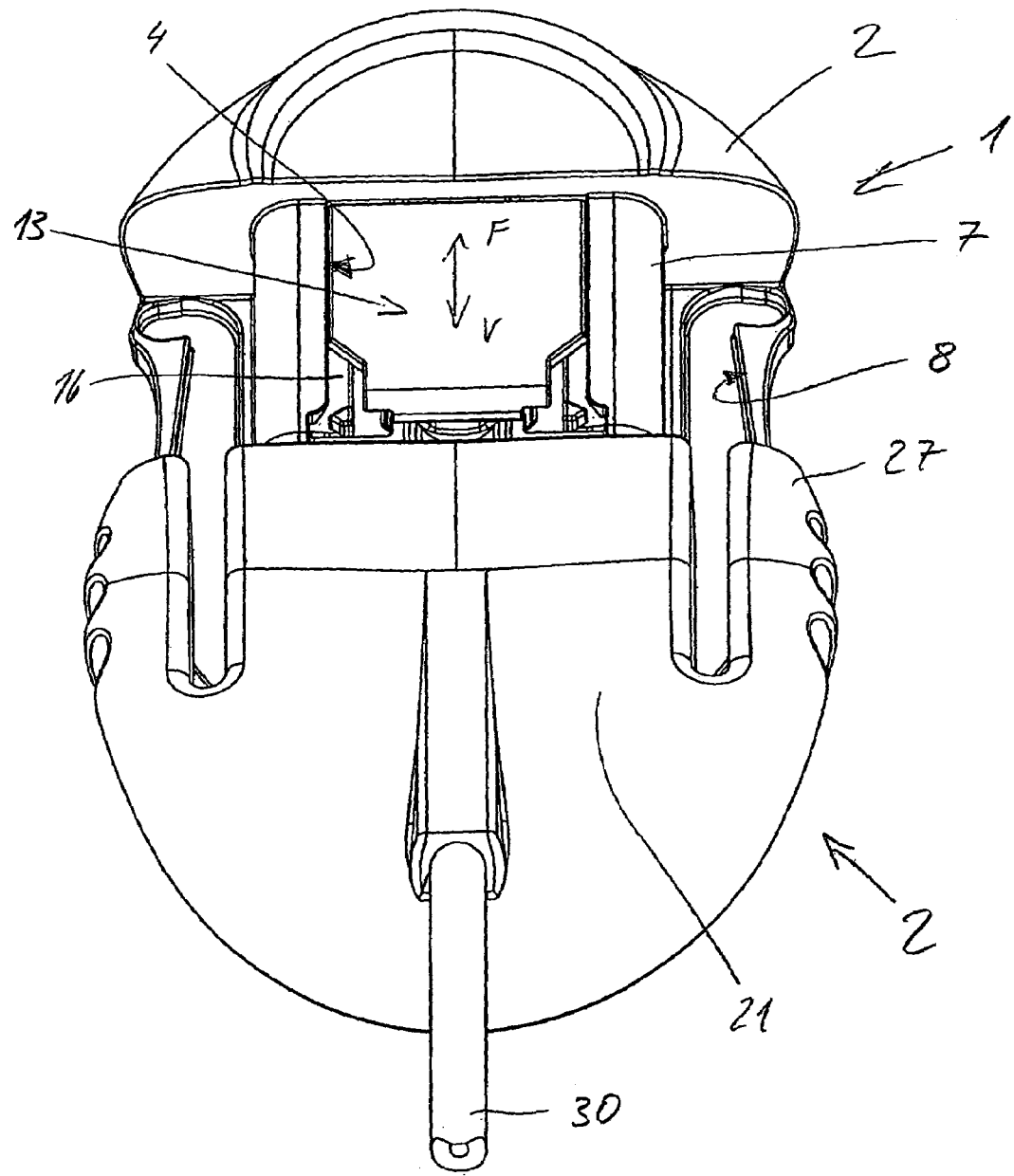
FIG. 9 shows the base body and the connecting body placed on the base body, before connection.

In the connected state, the base body 1 and the connecting body 20 are locked together to prevent accidental disconnection. The locking elements of the base body 1 are formed by two guide tracks 8 which each form a locking shoulder at their front ends pointing in direction F. The guide tracks 8 can be clearly seen in FIGS. 8 and 9, for example. They are formed in a rear, flat area of the housing 2 of the base body 1, in each case by an outer side wall of two recesses extending in direction F, which is open on the top face of the flat area of the housing 2 to the push-on connecting body 20. The locking elements of the connecting body 20 are two cams 28 (FIG. 5) which protrude from the underside of the connecting body 20 and, upon pushing-on, protrude into the respectively associated one of the recesses. The locking elements 28 of the connecting body 20 protrude from wings 27 which form actuating elements of the connecting body 20. The wings 27 protrude in a flexurally elastic manner from a main body of the housing 21 and can be bent toward one another the elastic restoring forces. The guide tracks 8 for the locking elements 28 point toward one another, for example obliquely, from their rear end as seen in direction F, so that the wings 27 are bent elastically toward one another by the locking elements 28 sliding along the guide tracks 8, when the connecting body 20 is pushed onto the base body 1. The locking shoulders of the guide tracks 8 are formed behind edges of the guide tracks 8, said guide tracks 8 suddenly widening outward at their front ends. When the connecting body 8 is pushed on, the wings 27 bending elastically toward one another gradually more strongly are therefore released outward again when their locking elements 28 have been moved out over the edge of the associated guide track 8. For disconnection, the user presses the two wings 27 toward one another so that their locking elements 28 is bent over the edges back into the associated guide track 8 and the connecting body 20 can therefore be drawn off again.

Since the connecting body 20 is guided by the base body 1 during connection, namely by means of the guide tracks 7 in the direction of movement of the slide element 13, the locking elements 28 are necessarily automatically guided along the guide tracks 8. During connection, the user therefore does not even have to hold the base body 1 when the base body 1 is fixed on the skin. The connecting body 20 also does not have to be held at the wings 27, and, in particular, the wings 27 do not have to be pressed together for connection. It suffices to slide the connecting body 20 on the base body 1. It is sufficient for the user to hold the connecting body 20 with one hand, for example at the transition between the connecting body 20 and the catheter 30, or on the catheter 30 alone. Moreover, the locking elements 28 preferably snap with an audible click into their catch position behind the edge of the respectively associated guide track 8. The user therefore hears whether the connecting body 20 is safely connected to the base body 1, in the illustrative embodiment whether the wings 27 are locked to the base body 1.

While exemplary embodiments, including preferred embodiments, of the present invention have been described herein, it is contemplated that various modifications could be made without deviating from the spirit of the present invention. Accordingly, it is intended that the scope of the present invention be dictated by the appended claims.

The invention claimed is:

1. A catheter head for medical and pharmaceutical applications, comprising a base body which can be positioned on organic tissue, and a connecting body which serves as fluid connector for the base body and has a fluid channel for forming the fluid connector, the base body and the connecting body detachably connectable, the base body comprising:
   a) a housing,
   b) a cannula protruding from the housing and serving for insertion into the tissue,
   c) a seal element held by the housing and having a connector face on which or via which the fluid channel of the connecting body can be placed in fluidic communication with the cannula, and
   d) a closure element supported by the housing having a closure surface complementary to the connector face of said seal element and movable relative to the seal element wherein, in a closure position, the closure element is in a proximal position relative to the seal element and seals the connector face of the seal element such that the closure surface covers the seal element connector face and, in an open position, is in a distal position relative to the seal element and opens the fluid channel of the connecting body.

2. The catheter head as claimed in claim 1, wherein the seal element has a passage extending from the cannula as far as the connector face of the seal element.

3. The catheter head as claimed in claim 2, wherein the connecting body forms an outlet nozzle with a free end at which the fluid channel of the connecting body opens into the passage of the seal element when the connecting body is connected to the base body.

4. The catheter head as claimed in claim 3, wherein the closure element is mounted in a displaceable manner.

5. The catheter head as claimed in claim 1, further comprising a lock element associated with the housing and a lock element associated with the closure element, said lock elements engaged in the closure position to prevent a movement of the closure element into the open position.

6. The catheter head as claimed in claim 5, wherein at least one of the lock elements is elastically resilient in a direction away from the engagement.

7. The catheter head as claimed in claim 6, wherein the connecting body, upon connection to the base body, moves the elastically resilient locking element out of engagement.

8. The catheter head as claimed in claim 1, further comprising a driver associated with the connecting body and a driver associated with the closure element, said drivers engaging when the connecting body is connected to the base body, the engagement having the effect that the connecting body, in a movement it makes relative to the base body upon connection, drives the closure element into the open position.

9. The catheter head as claimed in claim 1, further comprising a driver associated with the connecting body and a driver associated with the closure element, said drivers engaging when the connecting body is detached from the base body, the engagement having the effect that the connecting body, in a movement it makes relative to the base body upon detachment, drives the closure element into the closure position.

10. The catheter head as claimed in claim 9, wherein at least one of the drivers is formed on an elastically resilient snap-in catch and the drivers come into driving engagement via the elastic resilience of the snap-in catch, at least when the connecting body is connected to the base body.

11. The catheter head as claimed in claim 8, wherein the driver of the connecting body drives the closure element into and out of the open and closure positions.

12. The catheter head as claimed in claim 11, wherein the closure position of the closure element is an abutment position.

13. The catheter head as claimed in claim 12, wherein the open position of the closure element is an abutment position.

14. The catheter head as claimed in claim 1, wherein the connecting body and the base body are guided in translation on one another when they are being connected to one another and when they are being detached from one another.

15. The catheter head as claimed in claim 14, wherein the connecting body and the base body are guided on one another and in that they are centered on one another when they are being connected to one another.

16. The catheter head as claimed in claim 15, wherein, between the closure position and the open position of the closure element, the connecting body and the closure element are guided movably in the same direction from the base body.

17. The catheter head as claimed in claim 1, wherein the connecting body comprises at least one flexurally elastic wing which locks in a flexurally elastic manner with the base body when the fluid channel of the connecting body is connected to the cannula.

18. The catheter head as claimed in claim 17, wherein the base body and the wing form a guide track and an engagement member which, upon connection of the connecting body to the base body, is guided on the guide track, the engagement member protruding from one of the wing or the housing transversely with respect to the direction of the flexural elasticity of the wing.

19. The catheter head as claimed in claim 18, wherein the guide track forms a locking shoulder behind which the engagement member locks when the fluid channel of the connecting body is connected to the cannula.

20. A catheter head comprising a base body and a connecting body which serves as fluid connector for the base body and has a fluid channel for forming the fluid connector, the base body and the connecting body detachably connectable, the base body comprising:
   a) a housing;
   b) a cannula protruding from the housing;
   c) a seal associated with the housing and having a connector face for operably coupling to the fluid channel whereby the fluid channel is placed in fluidic communication with the cannula; and
   d) a closure supported by the housing having a substantially planar covering surface and movable relative to the seal wherein, in a closure position, the closure is in a proximal position relative to the seal and covers the connector face of the seal element via the substantially planar covering surface and, in an open position, is in a distal position relative to the seal andopens the fluid channel of the connecting body.

21. The catheter head of claim 20, further comprising a driver associated with the connecting body, said driver driving the closure into and out of the open and closure positions.

22. The catheter head of claim 20, further comprising a driver associated with the connecting body and a driver associated with the closure element, said drivers engaging when the connecting body is connected to the base body, the engagement having the effect that the connecting body, in a movement it makes relative to the base body upon connection, drives the closure element into the open position, and said drivers engaging when the connecting body is detached from the base body, the engagement having the effect that the connecting body, in a movement it makes relative to the base body upon detachment, drives the closure element into the closure position.

23. The catheter head as claimed in claim 22, wherein at least one of the drivers is formed on an elastically resilient snap-in catch and the drivers come into driving engagement via the elastic resilience of the snap-in catch, at least when the connecting body is connected to the base body.

24. A catheter head for medical and pharmaceutical applications for forming fluidic communication between a connecting body and organic tissue comprising:
   a housing;
   a fluid channel comprising:
      a cannula protruding from the housing for insertion into the tissue; and
      a seal element held by the housing and having a connector face on which or via which the connecting body can be placed in fluidic communication with the cannula; and
   a substantially planar closure element independent from said fluid channel and supported by the housing, said substantially planar closure element movable relative to said seal element and having an open position and a sealed position relative to the seal element, wherein in a sealed position, the substantially planar closure element is in a proximal position relative to the seal element and covers the connector face of the seal element and, in an open position, is in a distal position relative to the seal element and opens the fluid channel of the connecting body.

25. The catheter head of claim 24, wherein when the substantially planar closure element is in the sealed position, said fluid channel is sealed preventing fluidic communication with organic tissue.

26. The catheter head of claim 24, wherein when the substantially planar closure element is in an open position, said fluid channel is open and connected to said connecting body enabling fluidic communication with organic tissue.

27. The catheter head of claim 24, further comprising a lock element associated with the housing and a lock element associated with the substantially planar closure element, said lock elements engaged in the closure position to prevent a movement of the substantially planar closure element into the open position.

28. The catheter head of claim 24, further comprising a driver associated with the connecting body, said driver driving the substantially planar closure element into and out of the open and closure positions.

29. The catheter head as claimed in claim 1, wherein the closure element comprises a raised area on an underside extending toward the connector face of the seal element when said closure element is in a closure position such that a pressing force is created between the raised area and the connector face sufficient to hold the closure element in the closure position.

30. A catheter head for medical and pharmaceutical applications, comprising a base body which can be positioned on organic tissue, and a connecting body which serves as fluid connector for the base body and has a fluid channel for forming the fluid connector, the base body and the connecting body detachably connectable, the base body comprising:
   a) a housing, b) a cannula protruding from the housing and serving for insertion into the tissue,
c) a seal element held by the housing and having a connector face on which or via which the fluid channel of the connecting body can be placed in fluidic communication with the cannula, and
d) a closure element supported by the housing, wherein the closure element comprises a raised area on an underside directed toward the connector face of the seal element and, when said closure element covers said seal element in a closure position, a pressing force is created between the raised area and the connector face sufficient to hold the closure element in the closure position.

31. A catheter head for medical and pharmaceutical applications, comprising a base body which can be positioned on organic tissue, and a connecting body which serves as fluid connector for the base body and has a fluid channel for forming the fluid connector, the base body and the connecting body being able to be connected to one another in a detachable manner, the base body comprising:
a) a housing;
b) a cannula protruding from the housing and serving for insertion into the tissue;
c) a seal element for the cannula which is held by the housing and which has a connector face opposite the cannula on which or via which the fluid channel of the connecting body can be placed in fluid communication with the cannula; and
d) a closure element which is supported by the housing, is configured as a cover for the seal element and is linearly displaceable parallel to the seal element, the closure element, in a closure position, sealing off the connector face of the seal element and, in an open position, opening the connector face of the seal element for the fluid channel of the connecting body.

* * * * *